US012133940B2

United States Patent
Rodriguez

(10) Patent No.: US 12,133,940 B2
(45) Date of Patent: *Nov. 5, 2024

(54) LUMINAIRE AND METHODOLOGIES FOR COMBINED VISIBLE ILLUMINATION AND DEACTIVATION OF BACTERIA

(71) Applicant: ABL IP HOLDING LLC, Conyers, GA (US)

(72) Inventor: Yan Rodriguez, Suwanee, GA (US)

(73) Assignee: ABL IP Holding LLC, Conyers, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/216,263

(22) Filed: Jun. 29, 2023

(65) Prior Publication Data
US 2023/0355827 A1 Nov. 9, 2023

Related U.S. Application Data

(60) Continuation of application No. 17/369,043, filed on Jul. 7, 2021, now Pat. No. 11,738,111, which is a
(Continued)

(51) Int. Cl.
*A61L 9/20* (2006.01)
*A61L 2/08* (2006.01)
(Continued)

(52) U.S. Cl.
CPC ............... *A61L 9/20* (2013.01); *A61L 2/084* (2013.01); *A61L 2/26* (2013.01); *H05B 45/20* (2020.01);
(Continued)

(58) Field of Classification Search
CPC ........ A61L 2/084; A61L 2/26; A61L 2202/14; A61L 2202/11; A61L 2/10; A61L 9/20;
(Continued)

(56) References Cited

U.S. PATENT DOCUMENTS

| 5,925,885 A | * | 7/1999 | Clark | ................. A61L 2/081 |
| | | | | 250/455.11 |
| 8,398,264 B2 | | 3/2013 | Anderson et al. | |

(Continued)

OTHER PUBLICATIONS

Entire patent prosecution history of U.S. Appl. No. 16/271,061, filed Feb. 8, 2019, entitled, "Luminaire and Methodologies for Combined Visible Illumination and Deactivation of Bacteria."
Entire patent prosecution history of U.S. Appl. No. 17/369,043, filed Jul. 7, 2021, entitled, "Luminaire and Methodologies for Combined Visible Illumination and Deactivation of Bacteria."

*Primary Examiner* — Sean E Conley
*Assistant Examiner* — Brendan A Hensel
(74) *Attorney, Agent, or Firm* — Buchanan Ingersoll & Rooney PC

(57) ABSTRACT

An example luminaire includes a white light source (e.g. LEDs emitting white light in a region of the CIE color chart within three Macadam ellipses below the black body curve) and a violet light source emitting light in a wavelength range of approximately 380 nm to 450 nm (e.g. 405 nm LEDs) for deactivating bacteria, such as Methicillin-Resistant *Staphylococcus aureus* (MRSA) on a surface exposed to illumination from the luminaire. A controller coupled to the sources pulses the violet light source at an irregular rate and interval over a time period to apply a deactivation dosage of the violet light to bacteria within range of the emissions. When ON, the violet source emits light for deactivating bacteria at an intensity higher than the concurrent intensity of the white light.

13 Claims, 7 Drawing Sheets

Related U.S. Application Data division of application No. 16/271,061, filed on Feb. 8, 2019, now Pat. No. 11,123,450.

(60) Provisional application No. 62/631,063, filed on Feb. 15, 2018.

(51) Int. Cl.
 *A61L 2/26* (2006.01)
 *H05B 45/20* (2020.01)
 *H05B 47/115* (2020.01)

(52) U.S. Cl.
 CPC ......... *H05B 47/115* (2020.01); *A61L 2202/11* (2013.01); *A61L 2202/14* (2013.01)

(58) Field of Classification Search
 CPC ...... H05B 45/10; H05B 47/115; H05B 45/20; H05B 47/105
 See application file for complete search history.

(56) References Cited

U.S. PATENT DOCUMENTS

| | | | |
|---|---|---|---|
| 9,039,966 | B2 | 5/2015 | Anderson et al. |
| 9,333,274 | B2 | 5/2016 | Peterson et al. |
| 9,439,989 | B2 | 9/2016 | Lalicki et al. |
| 9,662,409 | B2 | 5/2017 | Rains, Jr. et al. |
| 9,700,641 | B2 | 7/2017 | Hawkins et al. |
| 9,820,361 | B1 | 11/2017 | Turvy, Jr. et al. |
| 2016/0093412 | A1 | 3/2016 | Liao et al. |
| 2016/0121007 | A1 | 5/2016 | Dayton |
| 2016/0375161 | A1 | 12/2016 | Hawkins et al. |
| 2016/0375162 | A1 | 12/2016 | Marry et al. |
| 2016/0375163 | A1* | 12/2016 | Hawkins ............. F21V 33/0068 422/22 |
| 2017/0173195 | A1 | 6/2017 | Stibich et al. |

* cited by examiner

LUMINAIRE AND METHODOLOGIES FOR COMBINED VISIBLE ILLUMINATION AND DEACTIVATION OF BACTERIA

RELATED APPLICATION

This application is a Continuation application of U.S. application Ser. No. 17/369,043, filed Jul. 7, 2021, which is a Divisional application of U.S. application Ser. No. 16/271,061, filed Feb. 8, 2019 (now U.S. Pat. No. 11,123,450, issued Sep. 21, 2021) which claims the benefit of U.S. Provisional Application No. 62/631,063, filed Feb. 15, 2018, entitled Luminaire and Methodologies for Combined Visible Illumination and Deactivation of Bacteria, the disclosures of which are entirely incorporated herein by reference.

TECHNICAL FIELD

The examples discussed herein relate to luminaires, lighting systems and/or lighting techniques for providing a combination of light for general illumination and light for deactivating a bacteria.

BACKGROUND

In recent years, there have been various proposals to incorporate, in general lighting equipment, light sources specifically configured to deactivate bacteria on a surface, such as Methicillin-Resistant *Staphylococcus Aureus* (MRSA) on work surfaces, sinks, floors etc. of hospitals, nursing homes or the like. Some proposals have used a single source to generate somewhat white light and light specifically configured to deactivate bacteria, in a manner such that the combined light is suitable for general illumination. Other proposals have incorporated white light sources and disinfection light sources together in one luminaire, including some implementations with independent intensity control of the two different types of sources. However, there is room for still further improvement.

SUMMARY

The examples combine white light from a first source and cleansing light from another source in one luminaire. The cleansing light is pulsed. For example, during each pulse emission, the output of the cleansing light may exceed intensity of concurrent white light emission.

For example, a disclosed system may include a luminaire and a controller. The luminaire includes a white light source, for general illumination, and a cleansing light source. The cleansing light source is configured to emit visible cleansing light of one or more wavelengths that deactivate a bacteria. The cleansing light source also is arranged so that emitted cleansing light is combined with the white light from the white light source. The controller is coupled to the light sources of the luminaire to control light emission from the white light source and light emission from the cleansing light source. The controller causes the cleansing light source to emit pulses of visible cleansing light at pulse times during white light emission from the white light source. During each pulse time of emission of a pulse of cleansing light from the cleansing light source, the controller controls the sources such that the intensity of pulse emission of the cleansing light from the cleansing light source is higher than the intensity of the white light emission from the white light source.

A method example may involve emitting white light from a first source in a luminaire. During the white light emission, the method also includes emitting pulses of visible cleansing light of one or more wavelengths that deactivate a bacteria, from a second source in the luminaire separate from the first source, for combination with the white light emission. During each pulse time of emission of a pulse of cleansing light from the second source, the intensity of pulse emission of the cleansing light from the second source is higher than the intensity of the white light emission from the first source.

In some more specific examples of a system or a method, the spectrum of the cleansing light has a maximum peak at a wavelength in a range of 380 nm to 450 nm. The white light may be within three Macadam ellipses below the Plankian Locus (black body curve) of the CIE color chart.

One or both of the light sources may be adjusted or otherwise controlled in response to one or more inputs. For example, a range sensor may enable the controller to adjust the intensity of pulse emissions of the cleansing light from the cleansing light source based on the detected range. By way of another example, use of an occupancy sensor may enable the controller to adjust the intensity of pulse emissions of the cleansing light from the cleansing light source based on detected occupancy/non-occupancy state. In yet another specific example, the controller is further configured to adjust one or more of ON/OFF state of combined light emission from the luminaire, the intensity of pulse emission of the cleansing light from the cleansing light source, or the intensity of the white light emission from the white light source, in response to an input received via the user interface.

Several specific examples of different techniques for controlling the cleansing light relative to the white light also are disclosed below. For example, the intensity of the white light emission from the first source may be maintained at least substantially constant over a time interval including emissions of a number of the pulses of the cleansing light from the second source. As noted, the cleansing light pulses, however, have intensity greater than the intensity of the white light.

In another example, the intensity of the white light emission from the first source is maintained at least substantially constant over each period between cleansing light pulse emissions from the second source, at a level sufficient for a desired degree of white light general illumination. However, at times of cleansing light pulse emissions from the second source, the intensity of the white light emission from the first source is lowered to a non-zero level such that combined emissions of white light and cleansing light are at a level sufficient for a desired degree of general illumination.

In a further example, one or more of the number of pulses, the pulse duration, or the pulse amplitude, of the cleansing light pulse emissions from the second source, over an interval of time, are controlled so that total cleansing light emission over the interval achieves a dosage expected to be sufficient to deactivate bacteria on a surface exposed to the pulses of cleansing emission.

Additional objects, advantages and novel features of the examples will be set forth in part in the description which follows, and in part will become apparent to those skilled in the art upon examination of the following and the accompanying drawings or may be learned by production or operation of the examples. The objects and advantages of the present subject matter may be realized and attained by means of the methodologies, instrumentalities and combinations particularly pointed out in the appended claims.

BRIEF DESCRIPTION OF THE DRAWINGS

The drawing figures depict one or more implementations in accordance with the present concepts, by way of example only, not by way of limitations. In the figures, like reference numerals refer to the same or similar elements.

DETAILED DESCRIPTION

Figure 1:
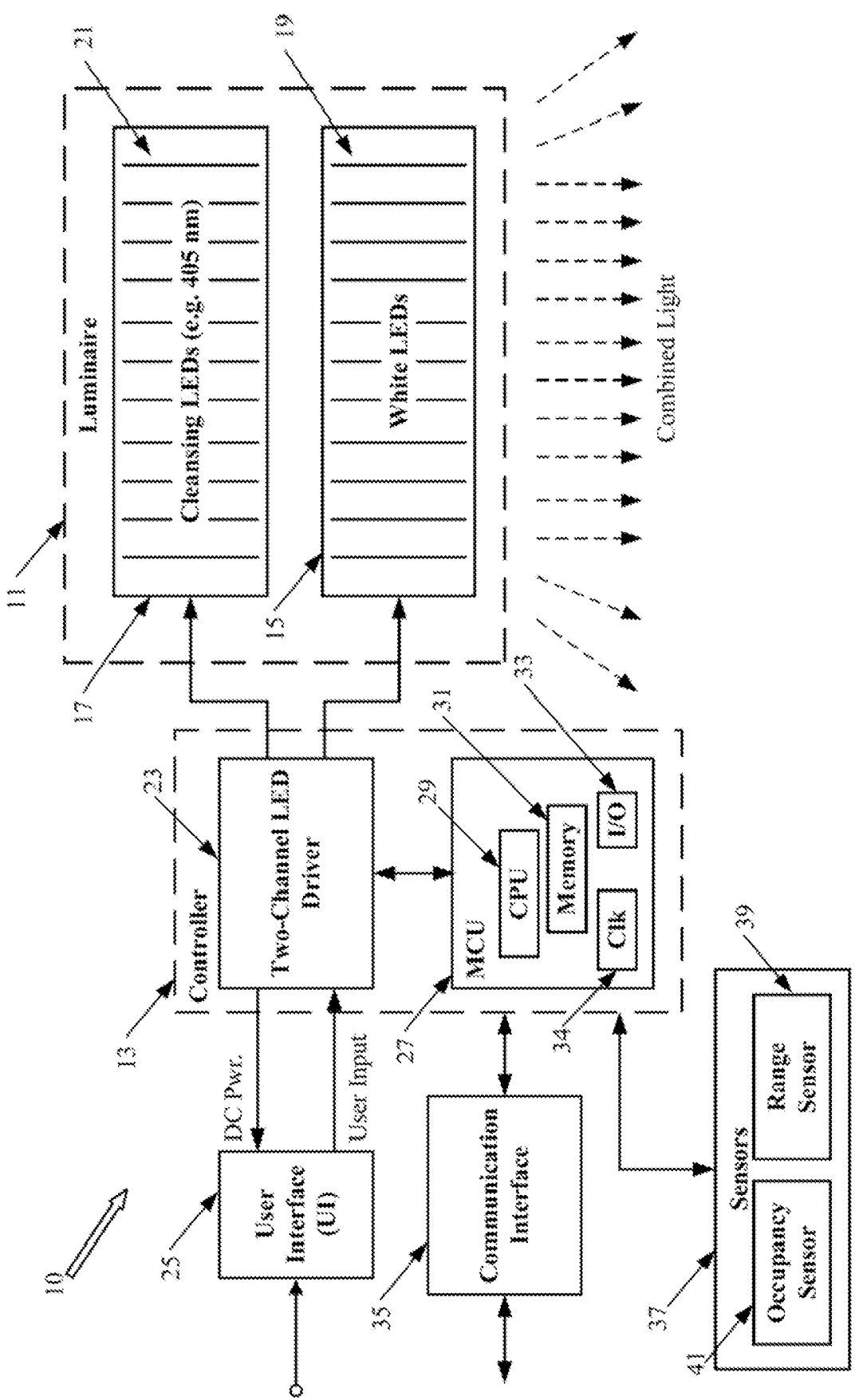
FIG. 1 is a simplified functional block diagram of a system for providing general illumination with bacteria cleansing light.

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, components, and/or circuitry have been described at a relatively high-level, without detail, in order to avoid unnecessarily obscuring aspects of the present teachings.

The examples below relate to improved hardware and techniques for combined general illumination and illumination with a cleansing light, that is to say, a light of a spectral characteristic expected to deactivate one or more types of bacteria. In a simple example, a system may include a luminaire and a controller. The luminaire includes a white light source and a separate cleansing light source. The controller may be incorporated in the luminaire or separate from the luminaire. Systems, however, may include some number of luminaires controlled by one controller or systems involving a number of networked controllers and luminaires associated with or incorporating the controllers.

The term "luminaire," as used herein, is intended to encompass essentially any type of device that processes energy to generate or supply artificial light, for example, for general illumination of a space intended for occupancy or observation, typically by a a human that can take advantage of or be affected in some desired manner by the light emitted from the device. However, a luminaire may provide light for use by automated equipment, such as sensors/monitors, robots, etc. that may occupy or observe the illuminated space, instead of or in addition to light provided for a human. In most examples, the luminaire(s) illuminate a space or area of a premises to a level useful for a human occupant in or passing through the space, e.g. general illumination of a room or corridor in a building or of an outdoor space such as a street, sidewalk, parking lot or performance venue.

The illumination light output of a luminaire, for example, may have an intensity and/or other characteristic(s) that satisfy an industry acceptable performance standard for a general lighting application. The performance standard may vary for different uses or applications of the illuminated space, for example, as between residential, office, manufacturing, warehouse, hospital, nursing home, or retail spaces.

Terms such as "artificial lighting," as used herein, are intended to encompass essentially any type of lighting that a device produces by processing of electrical power to generate the light. An artificial lighting device, for example, may take the form of a lamp, light fixture, or other luminaire that incorporates suitable light sources, where each light source by itself contains no intelligence or communication capability, such as one or more light emitting diodes (LEDs) or the like, or a lamp (e.g. "regular light bulbs") of any suitable type.

In several illustrated examples, such a luminaire may take the form of a light fixture, such as a pendant or drop light or a downlight, or wall wash light or the like. Other fixture type luminaire mounting arrangements are possible. For example, at least some implementations of the luminaire may be surface mounted on or recess mounted in a wall, ceiling or floor. Orientation of the example luminaires and components thereof are shown in some of the drawings and described below by way of non-limiting examples only. The luminaire with the lighting component(s) may take other forms, such as lamps (e.g. table or floor lamps or street lamps) or the like. Additional devices, such as fixed or controllable optical elements, may be included in the luminaire, e.g. to distribute light output from the light source in a particular manner.

Terms such as "lighting device" or lighting "system," as used herein, are intended to encompass essentially any combination of an example of a luminaire discussed herein with other elements such as electronics of a controller and/or support structure, to operate and/or install the particular luminaire implementation. Such electronics hardware, for example, may include some or all of the appropriate driver(s) for the illumination light source, any associated control processor or alternative higher level control circuitry, and/or data communication interface(s). The electronics for driving and/or controlling the lighting component(s) may be incorporated within the luminaire or located separately and coupled by appropriate means to the light source component(s) of the luminaire.

Light output from the luminaire, lighting device or lighting system may carry information, such as a code (e.g. to identify a luminaire or its location) or downstream transmission of communication signaling and/or user data. The light-based data transmission may involve modulation or otherwise adjusting parameters (e.g. intensity, color characteristic or distribution) of the light output from the white light source and/or of the light output from the cleansing light source.

It may be helpful to discuss a first system example with respect to FIG. 1. The lighting system 10 in the example of FIG. 1 includes a luminaire 11 and a controller 13. The luminaire includes a white light source 15, for general illumination, and a cleansing light source 17.

The white light source 15, in the example, is configured to emit white light within three Macadam ellipses below the Plankian Locus (black body curve) of the CIE color chart, although in some cases, white light sources having other white emission characteristics may be used. A variety of different types of light sources may be used to implement the white light source 15. In the example, the white light source utilizes an appropriate number of white LEDs 19 of a type and number typically used for general illumination, e.g. for a traditional white light indoor or outdoor illumination application.

The cleansing light source 17 is configured to emit visible cleansing light of one or more wavelengths that deactivate a bacteria. The cleansing light source 17 also is arranged so that emitted cleansing light is combined with the white light from the white light source. A variety of different types of light sources may be used to implement the cleansing light source 17. In the example, the cleansing light source 17 utilizes an appropriate number of violet LEDs 21 of a type and number such that pulsed operations thereof over a period or interval of time can supply an adequate dosage of cleansing light to inactivate bacteria. In the example, the violet LEDs 21 are 405 nm LEDs.

Each LED 19 is rated in the 380 nm to 450 nm range, which is sometimes referred to herein as violet. An example of a suitable LED that may be used for LEDs 19 is a 405 nm LED. Semiconductor devices such as the LEDs 19 exhibit emission spectra having a relatively narrow peak at a predominant wavelength, although some such devices may have a number of peaks in their emission spectra. Often, manufacturers rate such devices with respect to the intended wavelength of the predominant peak, although there typically is some variation or tolerance around the rated value, from device to device. For example, each LED 19 in the example of FIG. 1 may be rated for a 405 nm output, which means that it has a predominant peak in its emission spectra at or about 405 nm (within the manufacturer's tolerance range of that rated wavelength value) and emits wavelengths of light in some band around the predominant peak wavelength.

The controller 13 is coupled to the light sources 15, 17 of the luminaire 11 to control light emission from the white light source 15 and light emission from the cleansing light source 17. The controller 13 causes the cleansing light source 17 to emit pulses of visible cleansing light at pulse times during white light emission from the white light source 15. During each time of emission of a pulse of cleansing light from the source 17, the controller 13 controls the sources 15 and 17 such that the intensity of pulse emission of the cleansing light from the light source 17 is higher than the intensity of the white light emission from the light source 15.

In the example of FIG. 1 each source 15 or 17 includes a number of LEDs 19 or 21, and the controller 13 utilizes a two-channel LED driver. Any two-channel LED driver 23 that provides sufficient controllable power to drive the selected LEDs 19 and 21 may be used. Examples of suitable drivers 23 are available from eldoLED B.V. One of the control channel outputs of the driver 23 in connected to drive the LEDs 19 of the white light source 15, and the other of the control channel outputs of the driver 23 is connected to drive the LEDs 21 of the cleansing light source 17. Alternative implementations of the sources 15, 17 may have additional types of LEDs, e.g. an RGBW implementation of source 15 may have four types of independently controllable LEDs, for red (R), green (G), blue (B) and white (W). In such implementations of the luminaire 11, the driver 23 may be of a type having additional control channels for the additional types of LEDs.

Although not shown, the two channel driver 23 may receive power from AC mains, 100V AC to 488V AC, e.g. 120V AC or 220V AC. The driver 23, for example, may be a multi-volt input device capable of driving the LEDs using power obtained from any AC source in a range of 120V AC to 227V. It is also possible to implement the luminaire 11 with low voltage DC power supply, such as a 24V supply that hospitals utilize for magnetic resonance imaging (MRI) rooms in which ferromagnetic materials may not be permitted in the room with the MRI devices. As another alternative, the luminaire may use a battery power source, as an alternative or a backup to AC mains power. The circuitry of the device 10 may be located remotely from the luminaire 11, so that only the sources 15, 17 are included in the luminaire 11, and a remotely located driver 23 would connect to the LEDs 19, 21 to supply controlled current to drive the LEDs 19, 21.

The driver 23 in the example is directly responsive to an input from a user interface device 25 and exchanges data with a processor, which in the example is a microcontroller unit (MCU) 27 although a microprocessor or other type of processor circuitry may be used. In an implementation using an eldoLED driver as driver 23 of the system 10, the driver may supply DC power to the user interface device 25. The user interface device 25 may be a simple switch, a dimmer, a keypad, touchpanel etc. Depending on the implementation of the user interface 25, the controller may be configured, for example, to adjust one or more of ON/OFF state of combined light emission from the luminaire 11, the intensity of pulse emission of the cleansing light from the cleansing light source 17, or the intensity of the white light emission from the white light source 15, in response to an input received via the user interface 25. In other implementations using different types of drivers, the MCU may receive input from the user interface device 25 and control the driver 23 based on the received inputs.

The white light source 15 may be a fixed output device, or the source 15 may be dimmable from full ON to full OFF. The violet cleansing light source 17 is pulsed ON/OFF in accordance with a control algorithm, rather than being constantly ON at a particular level. The controller 13 in the example can vary the amplitude, frequency, time duration or width, phase or the like of the pulses of violet cleansing light output by the source 17. Such parameters of the pulses are controlled to achieve an average energy of the emitted cleansing light over a period of time, e.g. to achieve dosage of the cleansing light sufficient to deactivate a bacteria within range of the emission after passage of the period of time. The controlled pulse parameters may be constant over the period of time or may vary over the period of time algorithmically or in response to sensed conditions such as room occupancy or ambient light level. For example ten pulses of a timeframe having a long pulse ON duration may deliver the same average energy as 50 pulse or shorter ON duration in the same timeframe.

The driver 23 could be a relatively simple device, mainly with circuitry to selectively provide two control channel outputs with the minimum level of variability to implement a particular one of the cleansing and illumination algorithms described below based control from a higher level control element of the system, such as the MCU 27 in the example. Other driver implementations, such as intelligent drivers available from eldoLED, include more sophisticated driver circuitry as well as some internal logic circuitry and can support a wider range of modulation options selectable in response to commands from an MCU or other higher level logic circuit of the system 10.

In an LED based implementation of the luminaire 11, the LEDs 19 and the LEDs 21 may be mounted on one or more circuit board housed within the luminaire 11. In many cases, the LEDs 19 and the LEDs 21 will be on one circuit board, for example, intermingled at various locations on the board. The luminaire 11, however, may have separate circuit boards for the LEDs 19 and the LEDs 21, and/or may use two or more circuit broads for one or both sets of LEDs. The particular circuit board configuration, for example, may be adapted to the desired form factor of the luminaire 11 and/or to optimize heat dissipation from the LEDs 19 and the LEDs 21.

An MCU like that shown at 27 typically is a microchip device that incorporates the actual processor circuitry in the form of a central processing unit (CPU) 29 along with various memories 31 for storing instructions for execution by the CPU 29 as well as data having been processed by or to be processed by the CPU 29, and input/output ports (I/O) 33 for suitable connection/communication of the MCU 27 with other system elements. The example MCU also implements a clock (Clk) 34 for timing related functions. The clock 34 may be a specific circuit within the MCU 21 or implementing as a program controlled function of the CPU processor 29.

The CPU, any circuitry of the clock, the memory and the I/O of the MCU 27 typically are all included on a single chip and sometimes referred to as a "system on a chip" or SoC. Although shown separately, the elements of the MCU 27 may be incorporated on a chip with the two-channel LED driver 23 and/or with circuitry of a network communication interface 35. The memory 31 for example, may include volatile and non-volatile storage; and the program instructions stored in the memory 31 may include a lighting application (which can be firmware), in this example, for implementing the processor functions of the controller 13 relating to controlling the white light output and cleansing light output from the luminaire.

Figure 2:
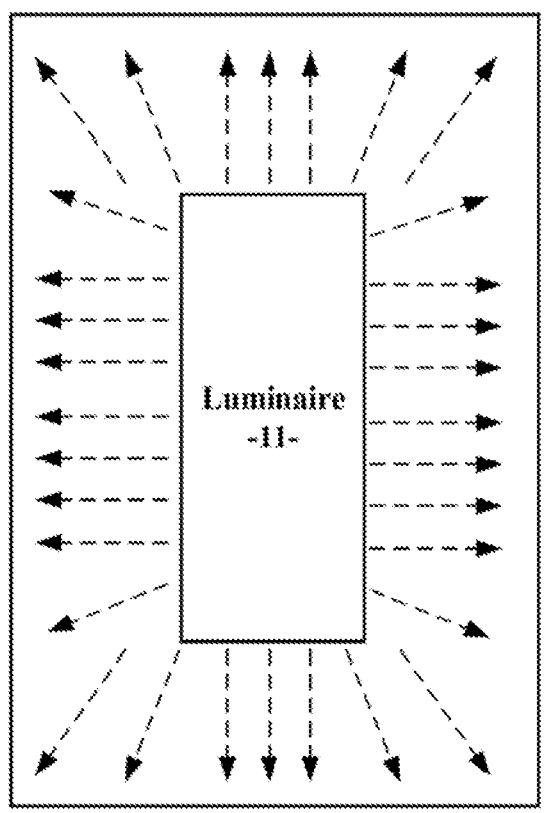
FIG. 2 is a plan view showing use of a luminaire of the type used in the system of FIG. 1 to provide combined general illumination and cleansing light in a room.

The example represents an arrangement in which one controller controls a single luminaire 11. FIG. 2 is a plan view showing use of a luminaire 11 of a system like the system 10 of FIG. 1. As shown in FIG. 2, the luminaire 11 provides combined general illumination and cleansing light in a room.

Figure 3:
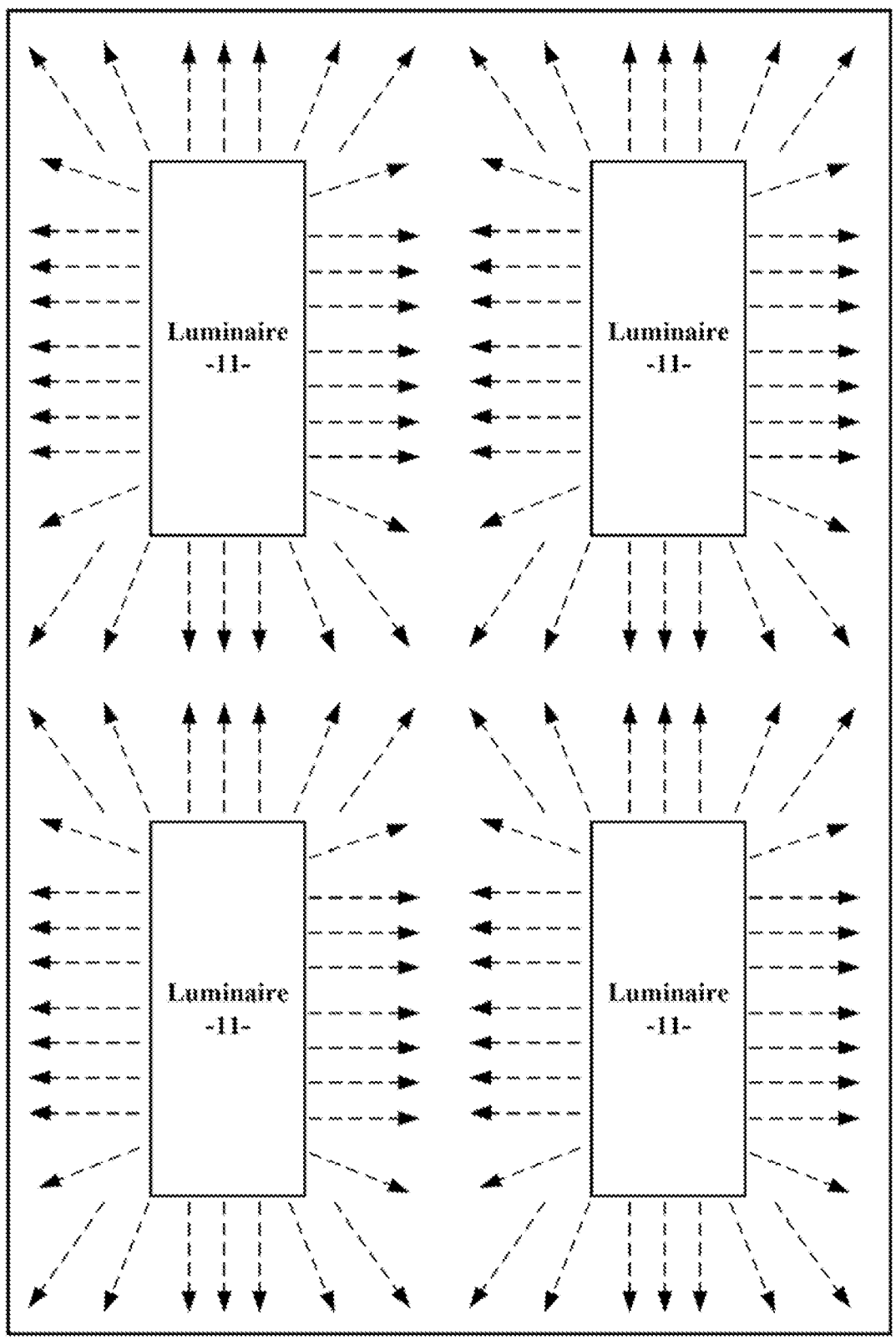
FIG. 3 is a plan view showing use of a number of luminaires of the type used in the system of FIG. 1 to provide combined general illumination and cleansing light in a room.

The system 10, however, may be easily modified to include and control a larger number of such luminaires. FIG. 3 is a plan view showing use of a number of luminaires 11 arranged in a ceiling or the like to provide combined general illumination and cleansing light in a room. There are a number of ways that a system 10 might be configured to have and control a number of luminaires 11, such as in an application like that of FIG. 3.

For example, the LED driver 23 (FIG. 1) may be expanded to provide two controlled drive channel outputs to the LEDs of the sources in each of one or more additional luminaires 11. In the example, the driver 23 is in the controller 13, which may be separate from the luminaire 11. In an alternate approach for unified processor control of a larger number of luminaires 11, each luminaire may include a two-channel LED driver, and one MCU or the like may control two or more such driver-integrated luminaires. It should also be apparent that the driver and MCU of the controller 13 and possibly the communication interface 35 may be implemented within the luminaire 11.

The communication interface 35 may be any communication device suitable for lighting related local communications between the system 10 and other similar systems, with common control equipment such as wall controllers or on-premises servers or gateway, or even with an external wide area network (WAN). The communication interface 35, for example, may be a network access card supporting wired connectivity over a data network, such as Ethernet, or may be a wireless transceiver compatible with a standardized wireless communication protocol, such as WiFi, Zigbee, personal area network (PAN) e.g. in the 900 MHz band, Bluetooth or Bluetooth Low Energy (BLE), LiFi, etc.

Network communications, for example, may allow operation of a neighboring number of luminaires (e.g. like in FIG. 3) for each of some number of zones in a large space, in a coordinated way to implement a cleansing and illumination algorithm of the type described herein. Some areas of the zone would have overlapping exposure from two or more luminaires, e.g. between adjacent luminaires or in the center of the area, whereas other areas of the zone around the periphery may have little or no overlapping exposure and receive light only from one of the luminaires. In such a scenario, the network communications allows the MCU or MCUs that control the luminaires of a particular zone to adjust operations of the various cleansing sources, e.g. to optimize cleansing light uniformity as much as feasible while insuring that all areas of the zone receive at least the minimum amount for the disinfection dosage.

Bacteria are sensitive to an overall applied energy of the cleansing light. The overall energy is a function of both intensity and accumulated ON time. Stated another way, the bacterial elements are effected by both a total time duration by the cleansing light and the amplitude or level of the cleansing light exposure. For example, if timeframe of 1 with an exposure amplitude 10 kills the exposed bacteria, it is reasonable to assume that an exposure of amplitude 5 kills the exposed bacteria after exposure for a timeframe of 2 or that exposure of amplitude 20 kills the exposed bacteria after exposure for a timeframe of 0.5. The controller 13 in the example can vary the amplitude, frequency, time duration or width, phase or the like of the pulses of violet cleansing light output by the source 17. Such parameters of the pulses are controlled to achieve an average energy of the emitted cleansing light over a period of time, e.g. to achieve dosage of the cleansing light sufficient to deactivate a bacteria within range of the emission after passage of the period of time.

The pulsing of the violet cleansing light from source 17 spreads the exposure duration. The pulsing also takes some of the violet component out of the combined light emitted from luminaire 11 to illuminate the space, e.g. so that the combined output light does not necessarily appear as violet in hue to a person occupying the illuminated space. The pulse rate, however, is fast enough that the human eye response does not cause the person to observe the pulsing as a perceptible flicker. For example, the pulsing may be at a rate higher than the typical human flicker fusion frequency, e.g. 30 Hz, 60 HZ, or 120 Hz or higher. Pulse frequencies of 70 HZ or higher are preferred although the upper end of the range may be relatively high, e.g. 800 HZ to 1,000 Hz or to 20,000 HZ or higher. As shown by way of several algorithms discussed in more detail later, the controller configuration allows considerable flexibility as to the manner in which the appropriate dosage of cleansing light is delivered within the particular time period.

When adjusting the overall light intensity of the combined light output from the luminaire 11, both white and cleansing types of light can be independently controlled. For example, the white may be dimmed with little or no concurrent dimming of the violet cleansing light from LEDs 21. If dimming lowers the intensity of the white too much without dimming the violet cleansing light, however, an increased relative violet component may make the overall illumination more violet and therefore less desirable to a human occupant. Such a result may be acceptable if desired to insure continued cleansing. At other times, it may be preferable to dim or turn OFF the violet light to maintain color quality of the relatively white luminaire output light, e.g. during a period when the desire for quality illumination outweighs the need for concurrent cleansing (as opposed to cleansing at a later time).

Returning to FIG. 1, output of one or both of the light sources 15, 17 may be adjusted or otherwise controlled in response to one or more sensed conditions. For that purpose the example system 10 of FIG. 1 also optionally includes one or more sensors 37.

A range sensor 39 may enable the controller 13 to adjust the intensity of pulse emissions of the cleansing light from the cleansing light source 17 based on the detected range, e.g. to the floor or a countertop surface or the like to be cleansed. The sensor 39 may be located in or near the luminaire to measure range of a surface or occupant from an output of the luminaire 11, from a ceiling or other surface on which the luminaire 11 is mounted, from a height of the luminaire 11 as mounted on or below a ceiling, or the like. The range sensor 39 may be a laser range finder, a radar device, a sonar device, an infrared emitter and detector aligned with a retroreflector at the surface to be sensed, a stereoscopic camera system or the like. An alternative to the range sensor 39 might use a camera to sense the amount of cleansing light reflected from different areas of the illuminated space.

If the system 10 does not include a range sensor, the system 10 may configured as part of the commissioning of the system at a particular installation, based in part of range determinations. The range information, instead of coming from a sensor in the system, would be separately provided, for example, from a commissioning device (not shown) in communication with the system 10 based on measurements done by or otherwise provided to the commissioning device. Various measurement and programming techniques may be used in commissioning, including to input data regarding range from the luminaire 11 to one or more surfaces to be cleansed by light from source 17. The range set-up as part of the commissioning process eliminates the added cost of the range sensor 39; but such an implementation of the system 10 is less dynamic, e.g. a change in room arrangement that changes the range to the surface may necessitate a new configuration operation by a technician or the like to adjust the range setting of the system.

Hence, the range sensor 39 (or a commissioned range setting) provides an indication of the distance from the luminaire 11 to the surface height in the room that is to be cleansed by the violet light from cleansing light source 17. For example, in an examination room, one luminaire 11 may be over an examining table whereas another luminaire 11 may be over a tile floor. In a dynamic implementation of system 10, each luminaire 11 may have an associated range sensor 39, or the luminaire over the floor may be set for a standard range, say to that to the floor but there is a sensor 39 associated with the luminaire over the examining table. In such an example, the luminaire over the table is controlled based on detection of range from the luminaire to the table top, say six feet. The system controls the luminaire over the floor based on programmed or sensed range from that luminaire to the floor, say nine feet.

To achieve a particular amount of illumination at a distance from a lighting device, e.g. for cleansing in the example, the light output from the luminaire 11 needs to be higher for larger separation distances (or can be lower for smaller separation distances). The variation of light at each surface may be inversely proportional to the square of the distance to the relevant surface from the particular luminaire. In the examination room examples, the system controls the source 17 providing respective cleansing light outputs of the two luminaires based on the different ranges. Over the period of time for the exposure dosage, the system provides a somewhat lower amount of cleansing light (e.g. less intense, fewer pulses, or shorter duration pulses) in the light output from the luminaire over the examination table than is provided in light output from the luminaire over the floor.

By way of another sensor example, use of an occupancy sensor 41. Although other types of occupancy sensing devices may be used as the sensor 41, a typical example uses a passive infrared (PIR) light detector or and associated processing circuitry or radar (e.g. ultra wide band) to determine occupancy status based on detection of motion or lack of motion detection for some set time. The occupancy sensor 41 may enable the controller 13 to adjust the intensity of pulse emissions of the cleansing light from the cleansing light source 17 based on a detected occupancy/non-occupancy state of a space illuminated by the combined light output from the luminaire 11. The controller 1 may also control ON/OFF state or intensity of light output by the white light source 15.

If the system detects motion in the room, the system may choose to optimize color quality of the combined relatively white light output of the luminaire. For that purpose, the system may reduce (e.g. by half) the amount of violet cleansing light or turn OFF the cleansing light source. To compensate, at another time when occupancy or motion is not detected in the room, the system can increase the intensity and/or pulse duration of violet cleansing light to still achieve the desired cleansing light exposure dosage by a particular time on a schedule.

With the network communications capability, either one or the other or both of the sensors may be in or associated with one luminaire 11 and the sensing results communicated via the network to other luminaires in a particular group or zone.

Figure 4:
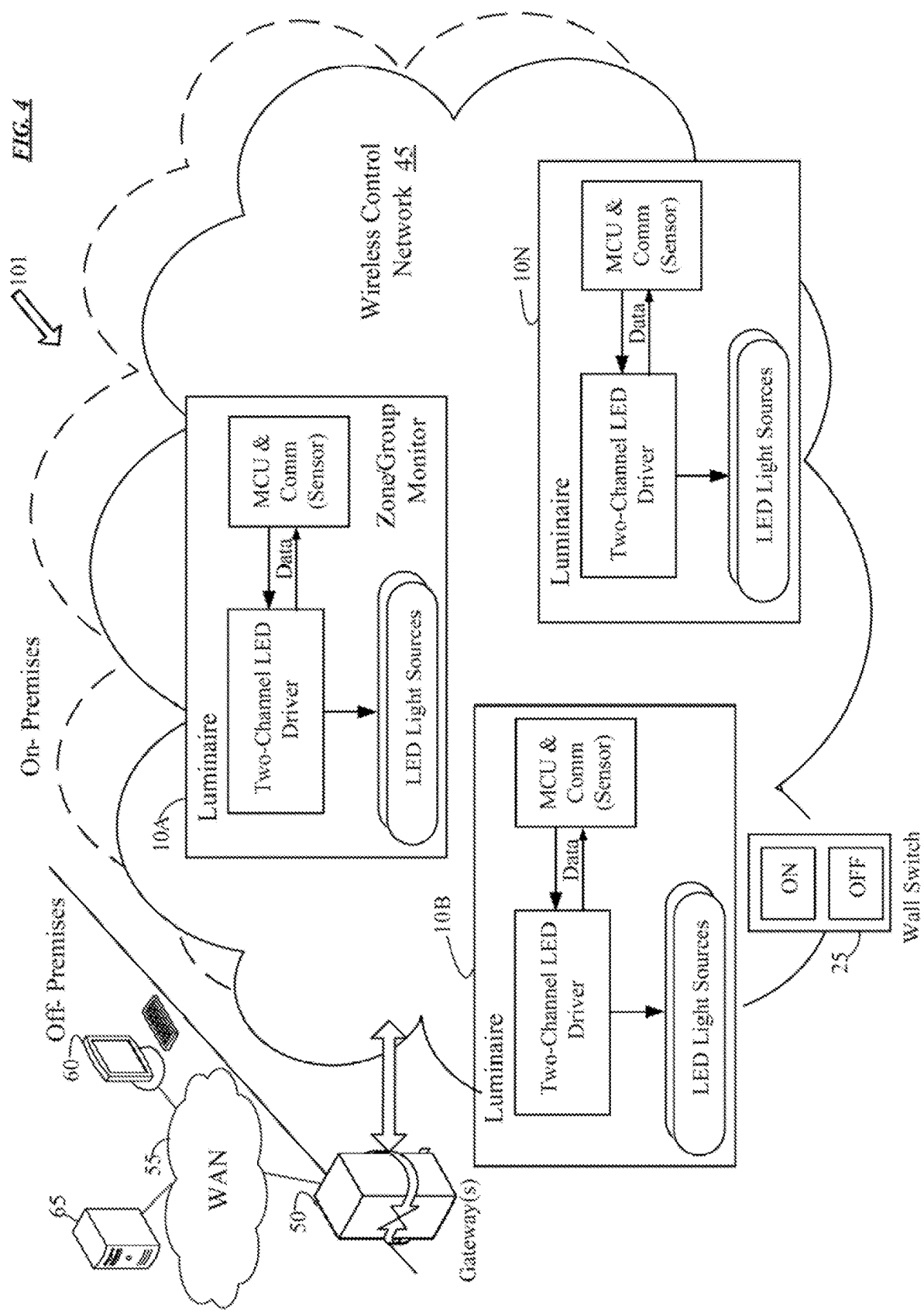
FIG. 4 is a functional block diagram of a networked set of lighting systems with most of the elements of each lighting system incorporated in the luminaires with the light sources and showing several other types of intelligent elements that may communicate with such lighting systems.

The example of FIG. 1 mainly depicted a single system/source implementation, although several modifications to control additional luminaires/light sources were briefly discussed. The combined illumination and cleansing may be implemented in a variety of other source and controller implementations, particularly if intended for coordinated operations and/or monitoring thereof in a large installation, such as a hospital, rehabilitation facility, or nursing home. FIG. 4 illustrates, in functional block diagram form, a networked system 101 including a set of lighting systems 10A to 10N. In the example, each of the lighting systems 10A to 10N incorporates most of the elements of system 10 of FIG. 1 into each luminaire with the white and cleansing light sources. As shown, for example, each luminaire forming one of the lighting systems 10A to 10N includes the two sources and the two-channel driver; and each such system 10A to 10N includes a module incorporating the MCU and the communication interface (Comm). That module, in one or more of the lighting systems 10A to 10N optionally may incorporate one or more of the sensors discussed above relative to FIG. 1.

The system 101 includes a user interface device, which may be a simple switch, a dimmer, a keypad, touchpanel etc. In the example of FIG. 4, the user interface device is shown as a wall switch at 25 configured for ON/OFF control inputs from the user. Unlike the example of FIG. 1, however, the wall switch 25 is not connected directly to the drivers in the luminaire but instead is configured for data communications with the luminaires. Although not separately shown, the wall switch 25 may include an MCU and communication module similar to those in the luminaires 10A to 10N except configured to instead respond to and drive the user interface components (e.g. push buttons and indictor lights) of the wall switch 25.

Any suitable data communication technology may be used. The example of FIG. 4 illustrates an arrangement of system 101 that utilizes wireless data communications. For that purpose, communication interfaces in the lighting systems 10A to 10N and the wall switch 25 take the form of one or more wireless transceivers (including wireless transmitter and receiver circuitry and circuitry and data connections compatible with the MCU). Each such component 10A to 10N or 25 will include a wireless transceiver for lighting related communications, such as for control and/or operational reporting functions, and those transceivers together will form/operate as a wireless lighting control network 45.

The wireless transceivers and thus the network 45 may utilize the physical layer and others of the lower layers of a standardized wireless communication protocol, such as WiFi, Zigbee, personal area network (PAN) e.g. in the 900 MHz band, Bluetooth or Bluetooth Low Energy (BLE), LiFi, etc. Higher layers of the protocol stack may be specific to lighting, whether standardized or proprietary to the equipment of a particular lighting system vendor.

Although not shown, the lighting systems 10A to 10N and the wall switch 25 each may include one or more additional wireless transceivers, for backup communications or for additional communication functions, such as commissioning or configuration or maintenance.

The system 101 at the premises may be implemented in a standalone configuration, e.g. without gateway access to other systems, networks or computers. The example of FIG. 4, however, shows an implementation with a gateway 50 providing access to a wide area network (WAN) 55, such as an intranet or the Internet, outside the premises. The gateway 50 and WAN 55 provide network data communications access to other computers, such as user terminal 60 or server computer 65, for interactions thereof with one or more of the lighting systems 10A to 10N and/or the wall switch 25. The gateway 50 may have a network link at the premises to luminaires and wall switches of other systems 101 at the premises or may link via WAN 55 to/through other gateways with wireless network communications to luminaires and wall switches of other systems 101 at the same or other premises.

The example shows a single grouping of luminaires 10A to 10N and one or more standalone wireless user interface devices shown as wall switch 25A on the wireless network 45. There may be other similar groups on the same wireless network 45, e.g. if all other groups are located within range of the one gateway 50. The dotted line cloud in the drawing represents an additional wireless network similar to network 45, which would link one or more similar groups of luminaires and wall switches or the like at the premises to each other and to another gateway (not shown separately) within wireless range of the equipment of the additional group(s).

More information about an implementation of a networked system like system 101 of FIG. 4 may be found for example in U.S. Pat. No. 9,820,361 by Turvy, Jr., et al.

The particular examples utilize 405 nm LEDs 21 for the emitters of the cleansing light source 17 and white LEDs as the LEDs 19 of the white light source 15 to provide white light of a color characteristic, e.g. within three Macadam ellipses below the Plankian Locus (black body curve) of the CIE color chart. A controller coupled to the sources pulses the violet light source 17 at periodic intervals or at random times. When ON, the violet source 17 emits light for deactivating bacteria at an intensity higher than the concurrent intensity of the white light.

Exposing bacteria to violet light, in the 380 nm to 450 nm wavelength range, has previously been shown to deactivate bacteria. Using visible-wavelength light, such as in the violet region, is less harmful to humans or animals than using ultraviolet light, therefore violet light can be applied in a range of disinfection applications, such as disinfection of potential contact surfaces. The systems and operational methodology examples disclosed herein offer one or more improvements over prior technologies, some of which are outlined below.

A prior approach utilized a 405 nm illuminator only, and apparently did not also support general white light illumination. While this may be suitable for applications using the cleansing light only, e.g. involving direct application to a surface or material to be cleansed, use in a space that may need general illumination would require one or more general illumination type light devices in addition to the 405 nm disinfection device, which is not desirable in general lighting applications. Such an installation tends to be expensive and complex. The use of two light sources in one luminaire for the two different types of light, as in the examples discussed herein, improves over such a cleansing only source approach because the luminaire can provide both the disinfection and general illumination in one fixture or the like. Lighting designers and end users generally prefer ancillary lighting functions to be combined with the artificial lighting source in one fixture, so as to avoid the need to install additional luminaires for the special purpose function, for disinfection in this case.

Another prior approach implemented cleansing and general illumination with a single integrated source in the lighting device, such as an LED with a 405 nm chip together in one package with a phosphor to convert some of the 405 nm light to broader band visible light for combined white output. The efficiency of the single source is rather low, e.g. about 35-40 lumens per watt, whereas general illumination LED sources today offer an efficiency of 150 lumens per watt or higher. The two source approach herein may take advantage of the more efficient white light type source, and therefore is more acceptable for general light requirements that often are sensitive to commercial or government specified power requirements.

Also, with the single source approach, the ratio of white light to violet light is fixed based on the design of the source device. There is no way to independently control the cleansing light intensity relative to the white light intensity. For example, increasing output intensity for a desired higher level of general illumination may result in an unnecessarily higher or over exposure intensity of the cleansing light. If a fixture with this type of source is mounted too high above the surface to be cleaned, e.g. higher than the design specification, the fixture may not adequately expose the surface to cleansing light and thus may not effectively disinfect the surface as intended. The use of two light sources in one luminaire for the two different types of light, as in the examples discussed herein, improves over such a single source approach because the respective levels of the cleansing light and the white light may be independently controlled for different installation configurations, for different uses/conditions of illuminated spaces, etc.

Another prior proposal suggested use of a 405 nm source and another light source of light of wavelengths that are perceived as white light, but the white light source always emitted light at a higher intensity or illuminance than the cleansing light from the 405 nm light source. This restriction limits the ability to independently control the intensity of the two different types of light to achieve both effective disinfection at the surface level and variable degrees of general illumination over time. The techniques in the examples herein may independently vary the intensities of both types of light, and the pulse emission of the cleansing light may have an intensity above the white light intensity, which may allow more efficient operations for both general illumination and disinfection. Also, the techniques in the examples herein may be more readily adaptable, e.g. for dimming or other overall control, based on detected range to a surface to be cleansed, based on a preset or real-time detection of occupancy, etc.

The examples may include white light LEDs or the like emitting white light in a range from 2200° K to 8000° K. The LEDs 19 or other emitters of the white light source 15, in some examples, emit light at least one Macadam ellipse below the Plankian Locus, although the range may be from at or just below that curve to as much as three Macadam ellipses below the Plankian Locus. Humans tend to perceive white light that is one to three Macadam ellipses below the Plankian Locus, particularly in a range of 2700° K to 5000° K, as white and pleasant with a warmer tone due to a magenta component. Light above the Plankian Locus is perceived as somewhat blue or greenish and thus colder to the human observer.

An example of the combined lighting implementation of a system 10 or examples of similar systems 10A to 10N in a networked implementation may use LEDs or other light emitters of light of particular characteristics. In several examples, with reference for convenience to FIG. 1, the cleansing light source 17 is a violet light source emitting light in a wavelength range of approximately 380 nm to 450 nm (e.g. 405 nm LEDs) for deactivating bacteria. The white light source 15, for example, may use LEDs or other types of emitters configured to emit white light within three Macadam ellipses below the Plankian Locus (black body curve). It may be helpful to explain these parameters of the light outputs from the sources in somewhat more detail.

Figure 5A:
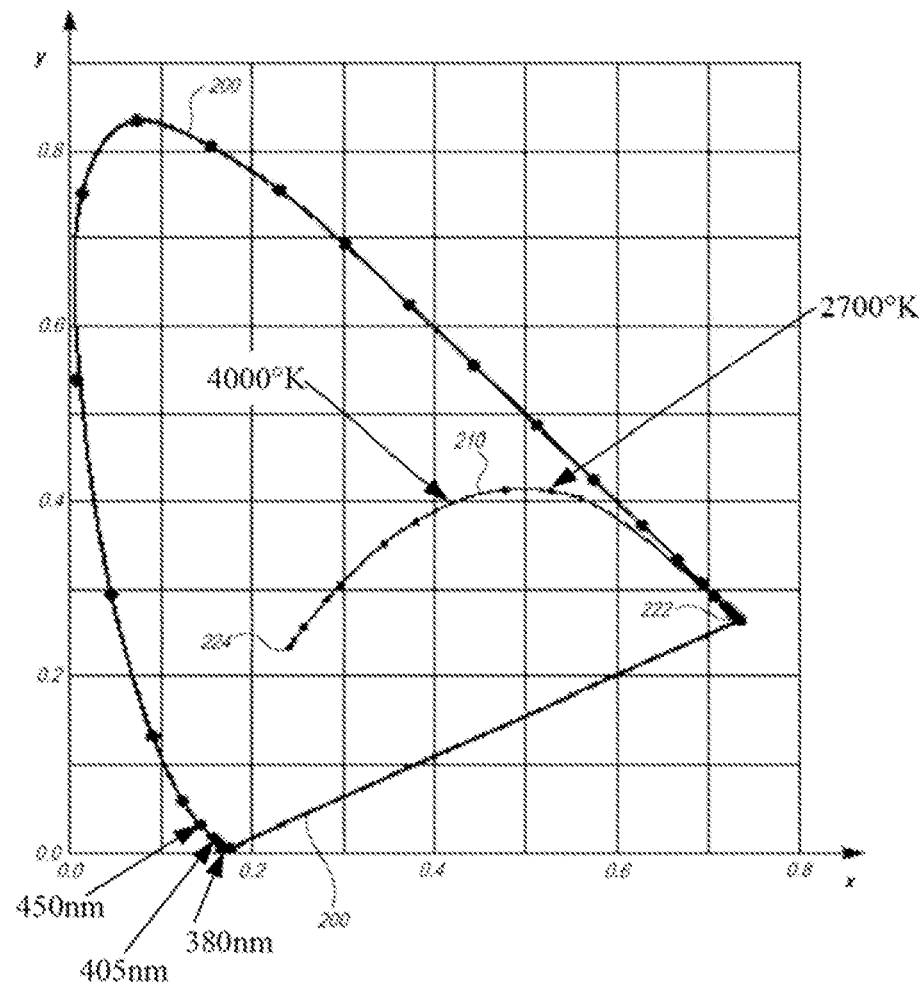
FIG. 5A is a simplified illustration of the CIE 1931 color chart useful in explaining color aspects of the light from the cleansing light source and the white light source in the luminaire of the system of FIG. 1.

FIG. 5A is a chromaticity diagram, in this example, a simplified version of the CIE 1931 color chart. In FIG. 5A, the horizontal x axis and the vertical y axis correspond respectively to the x, y chromaticity coordinates of a given point. Points along outline 200 correspond to completely saturated colors ranging from 360 to 700 nm, going clockwise from the bottom of the plot (around x=0.18, y=0) around to the right hand corner point (around x=0.73, y=0.26). The line connecting these two points represents a range of purple.

A curve 210 within outline 200 is the Plankian Locus, often referred to as the black body curve, of the CIE color chart. The Plankian locus corresponds to the peak wavelengths of distributions that are emitted by black bodies at correlated color temperatures (CCT) ranging from low, e.g., less than 500° K at the point labeled 222, to infinitely high, at the point labeled 224. A portion of the Plankian locus, e.g., color temperatures from around 2700° K to 6500° K generally corresponds to color perceived by humans as "white."

The cleansing light is a violet light in the range of 380 nm to 450 nm, along the lower left curve of the perimeter of the chart. The example cleansing source uses 405 nm LEDs. A particular cleansing light emission includes wavelengths of light at and around the particular nominal wavelength of the source, e.g. at and around the point corresponding to 405 nm.

Figure 5B:
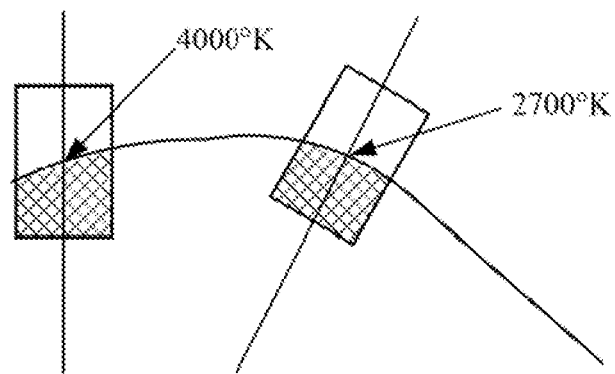
FIG. 5B is an enlarged view of a section of the color chart of FIG. 4, overlaid to help illustrate a more detailed example of the color characteristic light from the white light source in the luminaire of the system of FIG. 1.

The light from the white light source 15 is near a portion of the Plankian locus having a nominal color temperature in the range from around 2700° K to 6500° K. FIG. 5B represents an enlarged portion of the color chart of FIG. 5A including a section of the Plankian locus. For discussion purposes, we will consider an examples in which the white light source 15 emits light near the 2700° K point on the curve 210 or emits light near the 4000° K point on the curve 210.

In FIG. 5B, a central line passing through the curve at a point on the curve for 2700° K represents color coordinates that generally provide the 2700° K color temperature; and a central line passing through the curve at a point on the curve 4000° K represents color coordinates that generally provide the 4000° K color temperature. Distance from such a point on the blackbody curve may be measured as a difference or differential (Δ) in the 'u and 'v coordinates, sometimes referred to as Δuv. Above the black body curve, the Δuv is positive; and if large enough, light on a particular CCT line may be perceived by a human observer as somewhat greenish white. Below the black body curve, the Δuv is negative; and if large enough, light on a particular CCT line may be perceived by a human observer as somewhat magenta white.

A Macadam ellipse is a region on the color chart within which colors are indistinguishable from the color at the central point of the ellipse, to the eye of an average human observer. Macadam ellipses, however, change in size for different regions of the color chart. Generally, people see at most minor differences from a point on the black body curve if the actual color point of the light is within three Macadam ellipses of the point on the black body curve. In the example systems of FIGS. 1 to 4, the light from the LEDs 19 may be at a particular point on the Plankian Locus (black body curve) of the CIE color chart or even above the curve. In many cases described herein, however, the white light is at most three Macadam ellipses below the Plankian Locus (black body curve) of the CIE color chart.

Light below the black body curve, but within three Macadam ellipses of the curve, may be perceived as somewhat warmer white light than light just above the curve. Also, the added perception of warmth, helps to offset the cool perception of violet light during times when the violet cleansing LEDs 21 are operational.

The discussion of the color characteristics of the white LEDs 19, here refers to the overall light produced by the collection of white LEDs 19. Since light is additive, the group or set of LEDs may include LEDs of two or more different types with different characteristics. In such a case, however, the LEDs together would produce a white light output of the type described above, e.g. within three Macadam ellipses below the Plankian Locus (black body curve) of the CIE color chart. Also, the white source may be implemented with various combinations of LEDs or other sources that combine to produce the white light of the character described here, such as LED combinations of RGB, RGBA, RGBW, RGBAW, etc., or incandescent or other suitable types of light sources.

The driver 23 may be a circuit capable of providing a controllable constant current on each output channel to drive the respective sets of LEDs 17, 19. The current outputs of the two channels are controllable independently of one another. The MCU 27 or other higher level logic circuit instructs the driver to vary the outputs from the channels of the drivers and thus the current ratio and intensity ratio of cleansing to white light in accordance with an algorithm or operating procedure, several examples of which are described in more detail later. In the examples of combined illumination and cleansing, at least the drive current for LEDs 21 forming the cleansing source 17 is pulsed to provide a controllable pulsed cleansing light output from the luminaire 11. The drive current supplied to the white light source 15 and thus the white light output from source 15 may be relatively constant or may be pulsed in a controlled manner.

The system may implement an algorithm, for example, by appropriate programming and data stored in the memory 31 for execution and data processing by the CPU 29. The algorithm, for example, may monitor the time each luminaire is ON. The ON/OFF state of the luminaire and/or the dimming state of the luminaire output may be selected by the user, e.g. via a wall controller or an application on a user terminal device. If any sensors are provided, the algorithm also monitors the detections if any by the occupancy/motion sensor or the range sensor.

The duration of an intended disinfection cycle may be any length that is useful for disinfection control, e.g. one or more hours, one or more days, a week, or longer or shorter time duration. For purposes of an example, assume that the intended disinfection cycle time is each twenty-four hour day. Disinfection is controlled to achieve a cumulative exposure within each period of that cycle, reasonably expected to deactivate bacteria. Appropriate dosages are discussed in more detail in the literature, and the following example is given here for ease of discussion. For the hypothetical example, assume the intended dosage is 50% cleansing light output intensity over a total of 10 hours. Omitting units for simplicity, the cumulative dosage would be the integral over the cycle time of the intensity, which for constant output intensity over a continuous on-state would just be time multiplied by intensity or $10 \times 0.5 = 5.0$ in the hypothetical.

As noted, the MCU 27 monitors the state of the sources 15, 17 of the luminaire 11 and various sensed inputs and uses the clock 34 to monitor and control dosage over time. When the room is unoccupied, the algorithm may control the 405 nm LEDs 21 of the cleansing light source 17 to have a 50% on time duty cycle of the pulse light output and otherwise drive the LEDs 21 to their 100% intensity during pulse ON states, which results in a cumulative 50% cleansing light output per pulse waveform or per unit time. Assume first that the room remains unoccupied for 10 hours. In that simple scenario, the system 10 could achieve the desired cleansing light dosage of 5.0 cumulative output in 10 hours and may emit little if any cleansing light over the rest of the 24 hour cycle whether occupied or not. The times of such cleansing light emission while the room is unoccupied need not be consecutive.

In practice, the room may be used during any given 24 hour day such that it is only unoccupied for a smaller number of hours of the 24 hour day. The system can compensate by provide some cleansing light during occupancy and/or by increasing the duty cycle percentage during intervals of the day when the room is not occupied, to still achieve the intended cumulative dosage within the 24 hour day.

The clock and timer functions together with the occupancy sensing and knowledge of the controlled drive of the 405 nm LEDs at various times during the day enable the MCU 27 to adjust the cleansing light output to adequately provide the intended dosage. For example, when occupied, the MCU 27 may instruct the driver 23 to cause the LEDS 21 to reduce intensity during pulse ON states to 75% and/or reduce the duty cycle of the cleansing light pulses, to allow the combination of cleansing light with white light from the LEDs 19 to provide a desired quality of overall white illumination light. The cleansing light provided during the occupied state of the room still contributes towards achieving the intended disinfection dosage during the particular 24 hour day. In such a day, when the MCU 27 receives an indication that the room is not occupied, from the sensor 41, the MCU 27 may instruct the driver 23 to cause the LEDS 21 increase intensity during pulse ON states back to 100% and to increase the duty cycle of the cleansing light pulses to 50%, 75% or higher.

During the occupied state, if the user opted to dim the lights, the MCU may instruct the driver to adjust the ratio of output of the cleansing LEDs 21 to the outputs of the white LEDs 19, to meet the parameters of the algorithm for achieving the desired dosage over the 24 hour day. For example, if the algorithm indicates that a low cleansing light output may not be sufficient, the system can dim the overall light per the user input but adjust the ratios of outputs to provide a higher amount of cleansing light per pulse wavelength. This adjustment may degrade the color characteristic quality of the combined light, but in this scenario the algorithm sacrifices some quality of the combined light output for the improved ability to achieve the cleansing dosage. If the user request to dim the lights occurs at a time when the system has already achieved the dosage for the day or is projected by the algorithm to meet the dosage by the end of the day, the system may opt not to adjust the output ratio in favor of the cleansing light and maintain a higher overall color characteristic quality for the combined output light from the luminaire 11.

The intelligent control of the system in our example can implement a variety of different control schemes, for example, for different types of illuminated spaces. The control scheme, for example, may be different for each of an examination room, a hallway, a waiting room and/or a patient's room in different types of care units. If the illuminated space is part of a hallway, for example, the algorithm may implement a more deterministic scheme to average the quality of light and average the cleansing light parameter(s) over time so that the average cleansing light will achieve at least the intended dosage for the 24 hour day. For an examination room, where the quality of the light may be more important to the staff personnel when conducting examinations in the room, the algorithm used by the MCU would configure the system to provide at least a minimum level of light quality at all times when occupied but to provide a higher cleansing light (e.g. maximum pulse intensity and/or maximum % duty cycle) during all times when the room is unoccupied. For a waiting room that is intended for occupancy only during particular times of day, the algorithm used by the MCU may configure the system to provide a low amount of cleansing light during scheduled times for occupancy and a higher or maximum amount of cleansing light during times when the room is scheduled to be closed to business and therefore likely to be unoccupied.

In the examples, the cleansing light output of source 17 is pulsed in response to pulse current output from the channel of the driver 23; and the MCU 27 instructs the driver 23 to vary one or more of the pulse parameters (e.g. one or more of the number of pulses, the pulse duration, the pulse amplitude, the duty cycle, the pulse frequency, etc.) to increase or decrease the amount of cleansing light output from the LEDs 21 per unit time (e.g. per second or per minute), such that total cleansing light emission over a time interval achieves a dosage expected to be sufficient to deactivate bacteria on a surface exposed to the pulses of cleansing emission. The white light output is controlled by the MCU 27 via the driver 23 independently of the control of the cleansing light output. The algorithmic variations outlined above may be implemented using a variety of pulsing techniques relative to the cleansing techniques in combination with a variety of techniques for controlling light output from the white light source.

The combined illumination and cleansing examples discussed herein have some white light emissions when the system is emitting light from the cleansing light source 17, at least as would be perceived by a person in the illuminated space. In many examples, the white light is output from the LEDs 19 during the ON time of the pulses of the cleansing light output from cleansing LEDs 21 (e.g. in response to a particular level of a constant current drive signal from the channel of the driver 23). Even in control scheme examples in which the white light is pulsed, the pulsing of the white light is at a rate above typical flicker fusion frequencies (similar to the pulse rate of the cleansing light output). As a result, a human occupant would perceive the white light as constantly ON (free of perceptible flicker), even when the cleansing light source 17 is OFF.

In these ways, during cleansing light emissions there will always be some perceptible white light component of the output from the luminaire 11. When occupied, the combined light may appear as fairly good quality (e.g. high color rendering index "CRI and/or desirable coordinated color temperature "CCT"), although as noted the quality may be compromised somewhat if the algorithm determines a need to increase cleansing light output to achieve the intended dosage. When unoccupied, the cleansing light output may be increased to more readily achieve the intended dosage, but the system will still supplement the cleansing light output with a perceptible amount of light from the white light source 15, to avoid the impression by a person that may observe the room (e.g. upon entry or passing by an open door or a window into the room) that the room is being intensely decontaminated by violet light exposure, which might otherwise scare some people as to the danger of a bacteria in the room that might otherwise need to be eradicated by extreme treatment or create a fear that the cleansing like includes harmful ultraviolet components. The white light component, however, may be relatively low during unoccupied times of increased violet light exposure, for example, the white light output from the source 15 may 5% of the level utilized during normal occupancy/usage of the room.

Figure 6:
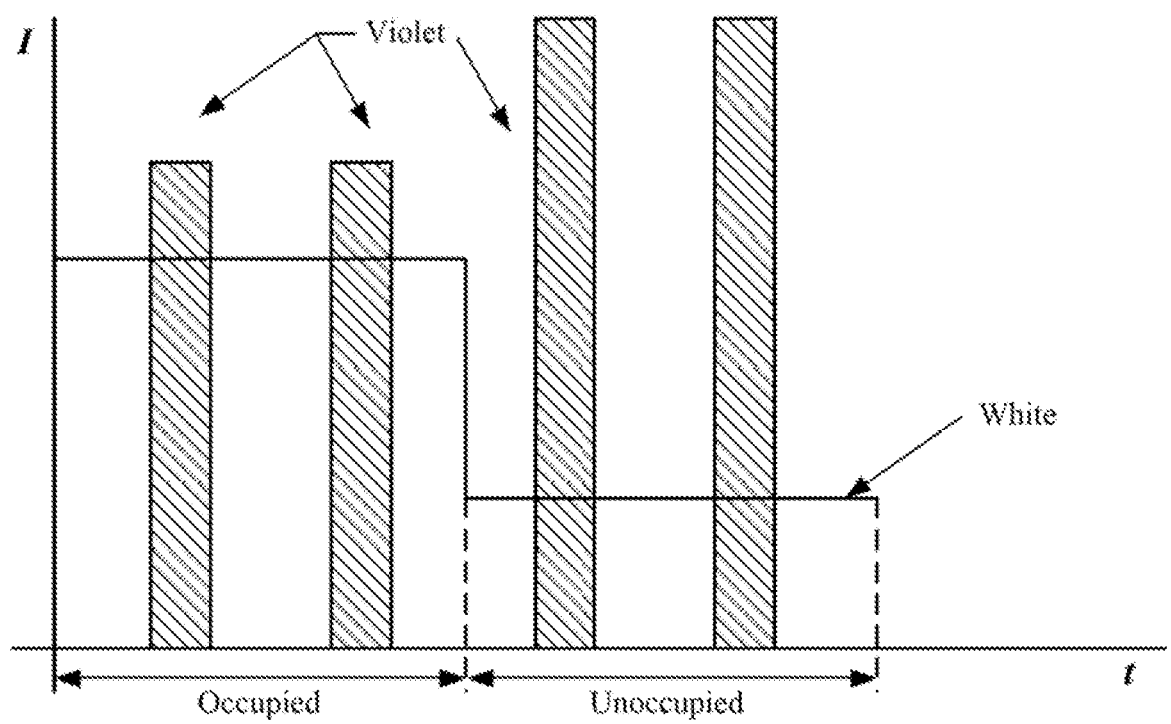
FIGS. 6 to 9 are various relative intensity diagrams showing various examples of intensity and timing relationships between white light emissions and cleansing light emissions from a luminaire or a system of luminaires.
Figure 7:
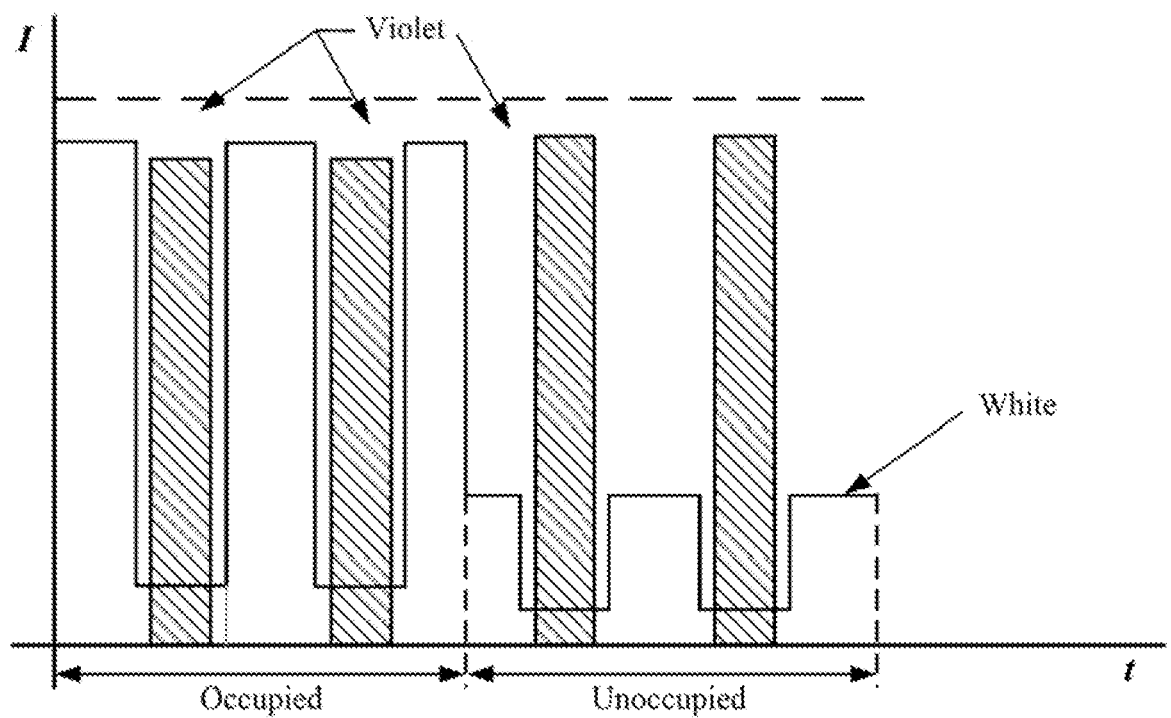
Figure 8:
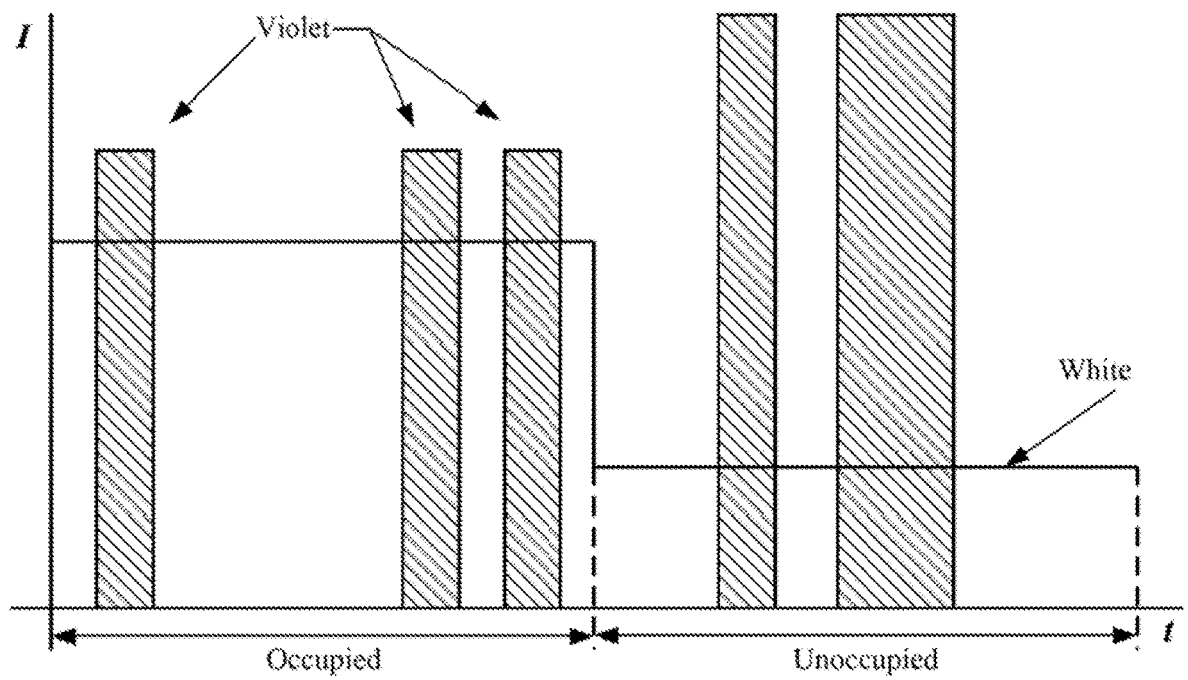
Figure 9:
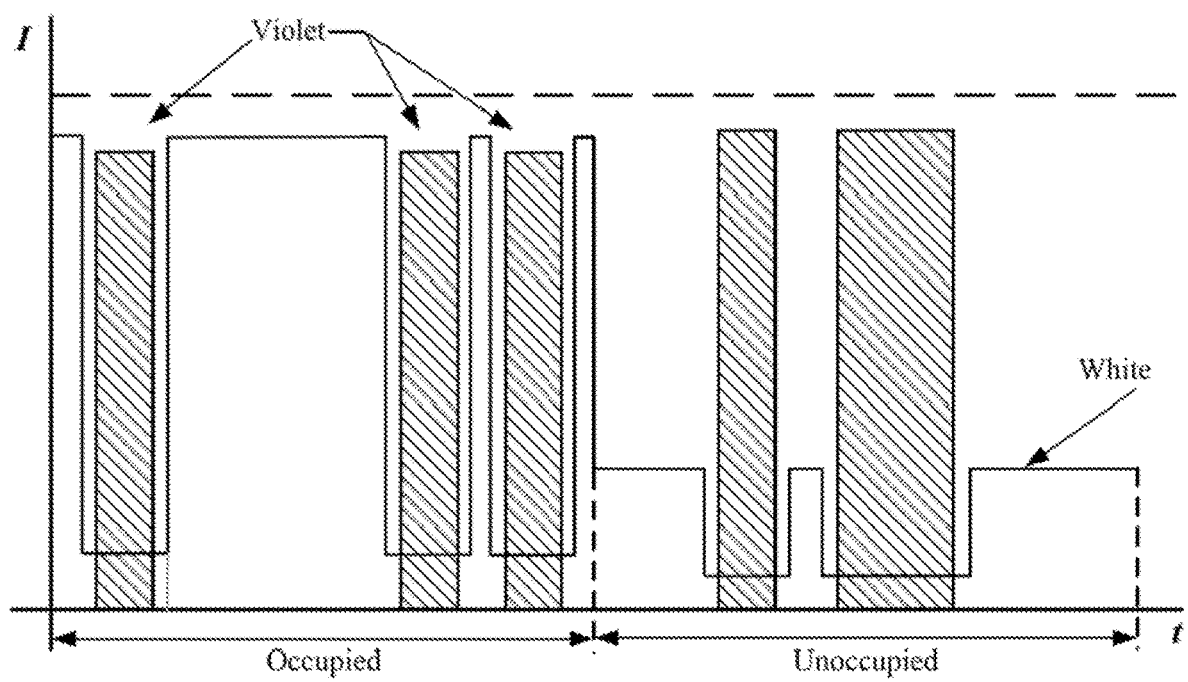

It may be helpful to consider several examples with regard to the graphs of FIGS. 6 to 9, which illustrate various relative intensities of the two components of light output and timing relationships between white light emissions and cleansing light emissions from a luminaire or a system of luminaires. In several of the examples, the cleansing light pulses are repetitively emitted at a constant rate and constant interval, over time, to apply a deactivating dosage of the cleansing light to any bacteria within range of the emissions, although other pulse parameters may be varied such as pulse duration/duty cycle or pulse intensity (see e.g. FIGS. 6 and 7). For convenience, FIGS. 6 and 7 show constant duty cycle but variation in pulse amplitude or intensity in different room states. In other examples the cleansing light pulses are emitted at random intervals but in sufficient number over a time period to apply a deactivating dosage of the cleansing light a bacteria within range of the emission (see e.g. FIGS. 8 and 9). FIGS. 8 and 9 also show variation in duty cycle.

With more specific reference to FIG. 6, the intensity of the white light emission from the first source is maintained at least substantially constant over a time interval including emissions of a number of the pulses of the cleansing light from the second source. The white light source 15 can be driven by a constant current output for the particular channel of the driver 23. For intensity control, the MCU 27 instructs the driver 23 to increase or decrease the driver current to the LEDs 19 of source 15 to increase or decrease the intensity of the white light output.

FIG. 6 shows the first scheme where the white light is constantly ON at a set level, and the system periodically adds a cleansing light pulse. In the occupied state, the white light is at a relatively high constant level, and when emitted, the amplitude of the violet light pulses is somewhat higher than the white light output amplitude. In the unoccupied state, the white light is still constantly ON but at a lower constant amplitude level. Again, in this second state, the amplitude of the violet light pulses is somewhat higher than the white light output amplitude. In the unoccupied state, however, the maximum amplitude of the violet light pulses is still higher than in the occupied state. The circuitry of the driver 23 may be configured to controllably vary the height or amplitude of the pulses which corresponds to instantaneous light output intensity (as shown), or the width of the pulse duration and thus the duty cycle, or the frequency of (and thus the spacing between) the pulses, or some other pulse parameter, or combinations one or more thereof.

In the example, the white light is shown as ON at a constant level for some time, then changed to a new level that remains constant for some time, and so on. This type of control may be implemented by controlling the DC current applied to drive the white light LEDs 19. The violet LEDs 21 forming the cleansing light source 17 may be pulsed by turning ON the DC drive current for those LEDs 21 at one power level, at each pulse time and otherwise turned completely OFF between pulses. The drive of the LEDs 19 of the white light source 15, and possibly the violet LEDs 21 of the cleansing light source 17, may also be modulated during the intervals when ON at a particular level. The drive of the LEDs 19 of the white light source 15, for example, may be pulse width modulated with variable duty cycles to provide dimming control.

In examples using the constant current control scheme for the white light, the white light will consume constant power while ON at a constant current level. When the system outputs a pulse of the cleansing light, during the ON time of that pulse, the driver 23 consumes additional power to also drive the cleansing LEDs 21. If the driver has a maximum combined output power limit, it may be necessary to limit the power applied to the white light to reserve some capacity for the additional driver power needed to generate the cleansing pulses. Although the control aspects that establish the relative amounts of light output over a period of time are independently controlled, it may be advantageous to control the relative timing of the pulses of the cleansing light and the white light to reduce the overlap of the white and cleansing pulse maximums to reduce the instantaneous power consumption. If there is no time overlap of the ON times of the pulses of the white and cleansing light pulses, and both are completely OFF in between pulses, then each channel may utilize the maximum instantaneous power capacity of the drive4 23. Alternatively, when the cleansing pulses are at maximum, the white light may be ON but at lower amplitude, which still makes more of the driver power available for the instantaneous cleansing light output.

In the example of FIG. 6, the white light source was driven by constant current to provide a relatively constant intensity output, although the level could be changed, e.g. for dimming or the like. FIG. 7 shows the alternative approach in which the white light output may be pulsed as well and control of the white light output may involve pulse parameter adjustment (e.g. amplitude, duty cycle, frequency, etc.) to increase or decrease the amount of white light output per unit time. In such an example, the intensity of the white light emission from the first source 15 is maintained at least substantially constant over each period between cleansing light pulse emissions from the second source 17, at a level sufficient for a desired degree of white light general illumination. At times of cleansing light pulse emissions from the second source 17, the intensity of the white light emission from the first source 15 is lowered to a non-zero level such that combined emissions of white light and cleansing light are at a level sufficient for a desired degree of general illumination.

FIG. 7 shows the second scheme in which the white light also is pulsed. The white light could be pulsed between a totally OFF state and a variable high/ON state, much like the cleansing light pulses. In the example, however, the drive current applied to the white LEDs 19 would have a positive direct current (DC) bias; and as a result, the low state of the pulsed white light does not fall to zero (full OFF) output state. The DC bias may be the same for different room states sensed by the system (e.g. occupied versus unoccupied) or may vary in response to different sensed room states.

In the example shown in FIG. 7, during ON times of the pulses of violet light output, the driver supplies some power to the white light source 15 based on the DC bias included in the drive channel output connected to the white LEDs 19. In both the example occupied and unoccupied room states, the cleansing light source 17 together with white light source 15 provide a combined light output of the luminaire 11 at or slightly below the dashed line in the drawing, which corresponds to the output intensity achievable in response to the maximum power available from the driver 23.

While the system 10 senses that a room is occupied, when pulsed at a high ON-state, the white light output intensity may be at an amplitude level at or near the maximum combined output corresponding to the maximum total drive power available from the driver 23, as represented by the dashed horizontal line in the drawing. In the unoccupied state, the high state of the white light output may be substantially lower than in the occupied state. In the occupied state, the white light intensity is reduced during the ON time of the violet pulses to a level corresponding to the DC bias of the applied drive current, as shown. Although the white light pulsing may be fully OFF during violet light pulse emissions, as shown, the lower level white still provides some white light output during violet light pulse emissions. In this case, the violet cleansing light pulse emission is at a higher level than the white light emission, during the ON times of the pulses of violet light output. The violet pulse emission may reach a level higher than the maximum of the white light emissions (when the violet light source is periodically OFF). In the example shown, the high level the violet pulse emissions in the occupied room state is not as high as the maximum of the white light emissions when the violet light source is periodically OFF in that room state. For times of violet pulse emissions in the occupied room state, the MCU 27 instructs the driver 23 to set maximum amplitude of the high level of the violet pulse emissions and the minimum amplitude of the low level the white violet pulse emissions in that room state so as combine to produce an overall luminaire output intensity at or slightly below a combined intensity corresponding to the maximum total drive power available from the driver 23, as represented by the dashed horizontal line. Similarly, in the unoccupied room state, the MCU 27 instructs the driver 23 to set maximum amplitude of the high level of the violet pulse emissions in the unoccupied room state and the minimum amplitude of the low level the white violet pulse emissions in that room state so as to combine to produce an overall luminaire output intensity at or slightly below a combined intensity corresponding to the maximum total drive power available from the driver 23, as represented by the dashed horizontal line.

This coordinated pulsed emission approach takes better advantage of the power available from the driver 23 during OFF times of the cleansing light output and may be implemented using a lower power driver than the earlier approach using constant current control for the white light and adding pulsed violet light emissions.

The examples of FIGS. 6 and 7 involved regular repetitive pulsing of one or both light sources. In typical schemes for controlling perceptible light levels using pulse modulation, e.g. pulse width modulation that controls the duty cycle of pulses that are emitted at a frequency typically above human eye flicker fusion frequency, the pulses are generated at a constant frequency and are periodic recurring waveforms. With such control schemes, adjustment of light output amounts can involve modulation of the pulse amplitude, frequency, duty cycle, or the like. As an alternative, the control scheme for either one or both of the cleansing light and the white light may utilize a random variation of pulse outputs. FIGS. 8 and 9 depict to example control schemes using random variations.

Consider the cleansing light by way of example, where achieving the dosage involves a cumulative light output (integral of the area under the pulse signal over time). The pulses need not be regular in timing or shape. A more randomized pulse scheme as in FIGS. 8 and 9 is less likely to be perceived as flicker than a regular pulsing of a light output, e.g. as used in pulse width modulation.

In FIG. 8, the white light varies between a high intensity level when the room is occupied and a low intensity level when the room is unoccupied, based on constant DC current in the two different room states, in a manner similar to the example of FIG. 6. In the approach of FIG. 8, however, the timing and duration of the violet pulses are randomized over time. The intensity of the violet pulses is higher than the intensity of the constant level of light output from the white light source, both when the room is occupied and when the room is unoccupied. In the unoccupied room state, however, the intensity of the violet pulses also is higher than the intensity of the violet pulses during the occupied room state.

The approach represented by FIG. 9 is more analogous to the pulse scheme of FIG. 7, except that the pulse timing and duration are randomized. In the example of FIG. 9, during the random ON times of the pulses of violet light output, the driver supplies some power to the white light source 15 based on a DC bias included in the drive channel output connected to the white LEDs 19. In both the example occupied and unoccupied room states, the cleansing light source 17 together with white light source 15 provide a combined light output of the luminaire 11 at or slightly below the dashed line in the drawing, which corresponds to the output intensity achievable in response to the maximum power available from the driver 23. In the approach of FIG. 9, the timing and duration of the violet pulses are randomized over time, and the timing and duration of low-state of the white light pulses are randomized in a corresponding manner.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," "includes," "including," or any other variation thereof, are intended to cover a non-exclusive inclusion, such that a process, method, article, or apparatus that comprises or includes a list of elements or steps does not include only those elements or steps but may include other elements or steps not expressly listed or inherent to such process, method, article, or apparatus. An element preceded by "a" or "an" does not, without further constraints, preclude the existence of additional identical elements in the process, method, article, or apparatus that comprises the element.

Unless otherwise stated, any and all measurements, values, ratings, positions, magnitudes, sizes, and other specifications that are set forth in this specification, including in the claims that follow, are approximate, not exact. Such amounts are intended to have a reasonable range that is consistent with the functions to which they relate and with what is customary in the art to which they pertain. For example, unless expressly stated otherwise, a parameter value or the like may vary by as much as ±10% from the stated amount.

In addition, in the foregoing Detailed Description, it can be seen that various features are grouped together in various examples for the purpose of streamlining the disclosure. This method of disclosure is not to be interpreted as reflecting an intention that the claimed examples require more features than are expressly recited in each claim. Rather, as the following claims reflect, the subject matter to be protected lies in less than all features of any single disclosed example. Thus the following claims are hereby incorporated into the Detailed Description, with each claim standing on its own as a separately claimed subject matter.

While the foregoing has described what are considered to be the best mode and/or other examples, it is understood that various modifications may be made therein and that the subject matter disclosed herein may be implemented in various forms and examples, and that they may be applied in numerous applications, only some of which have been described herein. It is intended by the following claims to claim any and all modifications and variations that fall within the true scope of the present concepts.

What is claimed is:

1. A method of illumination and deactivation of bacteria in an area, comprising:
    emitting white light from a first source in a luminaire in the area;
    during the white light emission, emitting pulses of visible cleansing light of one or more wavelengths that deactivate a bacteria, from a second source in the luminaire separate from the first source, wherein the emitted visible cleansing light is combined with the emitted white light from the first source and output from the luminaire; and
    during each pulse time of emission of a pulse of cleansing light from the second source, controlling the white light from the first source and the visible cleansing light from the second source such that for both a human-occupied state and a human-unoccupied state of the space illuminated by the luminaire, an intensity of pulse emission of the cleansing light from the second source is higher than an intensity of the white light emission from the first source,
    wherein the pulses of visible cleansing light are emitted at an irregular rate and interval over a time period to apply a deactivation dosage of the cleansing light to the bacteria within range of the emissions.

2. The method of claim 1, wherein the intensity of pulse emission of the cleansing light during the human-unoccupied state of the space is higher than the intensity of pulse emission of the cleansing light during the human-occupied state of the space.

3. The method of claim 1, further comprising emitting pulses of the white light from the first source in the luminaire at an irregular rate and interval.

4. The method of claim 1, wherein a pulse rate of the visible cleansing light is >70 Hz.

5. The method of claim 4, wherein the pulse rate is 70 Hz-1000 Hz.

6. The method of claim 4, wherein the pulse rate is 70 Hz-20,000 Hz.

7. The method of claim 1, wherein a spectrum of the cleansing light has a maximum peak at a wavelength in a range of 380 nm to 450 nm.

8. The method of claim 1, wherein the white light is within three Macadam ellipses below the Plankian Locus (black body curve) of the CIE color chart.

9. The method of claim 1, further comprising:
    sensing a range to a surface from which the bacteria are to be deactivated; and
    adjusting the intensity of pulse emission of the cleansing light from the second source based on the detected range.

10. The method of claim 1, further comprising:
    sensing an occupancy or non-occupancy state of the space illuminated by the combined emissions from the first and second sources; and
    adjusting the intensity of pulse emission of the cleansing light from the second source based on the detected state.

11. The method of claim 1, wherein the intensity of the white light emission from the first source is maintained at least substantially constant over a time interval including emissions of a number of the pulses of the cleansing light from the second source.

12. The method of claim 1, wherein:
    the intensity of the white light emission from the first source is maintained at least substantially constant over each period between cleansing light pulse emissions from the second source, at a level sufficient for a desired degree of white light general illumination; and
    at times of cleansing light pulse emissions from the second source, the intensity of the white light emission from the first source is lowered to a non-zero level such that combined emissions of white light and cleansing light are at a level sufficient for a desired degree of general illumination.

13. The method of claim 1, further comprising controlling one or more of a number of pulses, pulse duration, or pulse amplitude, of the cleansing light pulse emissions from the second source, over an interval of time, such that a total cleansing light emission over the interval of time achieves the dosage expected to be sufficient to deactivate bacteria on a surface exposed to the pulses of cleansing light emission.

* * * * *